United States Patent [19]
Weglicki

[11] Patent Number: 5,854,287
[45] Date of Patent: Dec. 29, 1998

[54] D-PROPRANOLOL METABOLITES USEFUL FOR ANTIOXIDANT ACTIVITIES

[76] Inventor: William B. Weglicki, 8404 Coach St., Potomac, Md. 20850

[21] Appl. No.: 807,449

[22] Filed: Feb. 28, 1997

Related U.S. Application Data

[60] Provisional application No. 60/012,633 Mar. 1, 1996.
[51] Int. Cl.[6] .......................... A61K 31/19; A61K 31/135
[52] U.S. Cl. ............................. 514/569; 514/652
[58] Field of Search ...................................... 514/652, 569

[56] References Cited

PUBLICATIONS

Chemical abstracts 117:184688u yu et al, 1992.
Weglicki, M.D. et al.—"Antioxidants and the Cardiomyopathy of MG–Deficiency"—The American Journal of Cardiovascular Pathology, vol. 4, No. 3, pp. 210–215 (1992).
Mak et al. —"Membrane Antiperoxidative Activities of $_D$Propranolol, $_L$Propranolol and Dimethyl Quaternary Propranolol (UM–272)"—Pharmacological Research, vol. 25, No. 1, pp. 25–30 (1992).
Nies, M.D. —"Noncardioselective β–Adrenoreceptor Blockers"—W.B. Saunders Company (Messerli–Cardiovascular Drug Therapy) —Chapter 32, pp. 420–435 (1990).
Kramer et al. —"Lipid Peroxidation–Derived Free Radical Production and Postischemic Myocardial Reperfusion Injury"—Cellular, Biochemical And Molecular Aspects of Reperfusion Injury, vol. 723 of the Annuls of the New York Academy of Science, pp. 180–196 (Jun. 17, 1994).
Mak et al. —"Antioxidant Activity of Calcium Channel Blocking Drugs"—Methods in Enzymology, vol. 234, pp. 620–631 (1994).
Mak et al. —"Beta–Blockers with Antioxidant Properties form Propranolol to Carvedilol"—Free Radicals Lipoprotein Oxidation and Atherosclerosis, pp. 457–471 (1995).
Mak et al. —"Inhibition of Sarcolemmal Carbon–Centered Free Radical Formation by Propranaolol"—Circulation Research, vol. 65, No. 4, pp. 1151–1156 ( Oct. 1989).
Weglicki et al.—"Mechanisms of Cardiovascular Drugs As Antioxidants"—Molecular and Cellular Cardiology, vol. 22, No. 10, pp. 1199–1208 (Oct. 1990).
Kramer et al. —"Lipid Peroxidation–Derived Free Radical Production and Postischemic Myocardial eperfusion Injury"—Cellular, Biochemical and Molecular Aspects of Reperfusion Injury, vol. 723 of the Annuls of the New York Academy of Science, pp. 180–196 (Jun. 17, 1994).
Chobanian et al. —"Effects of Propranolol on Atherogenesis in The Cholesterol–Fed Rabbit"—Cardiovascular Institute, and Evans Department of Clinical Research, Boston University School of Medicines, pp. 755–762 (Jan. 1985).
β–Blocker Heart Attack Trial Research Group—"A Randomized Trial of Propranolol in Patients with acute Myocardial Infarction"—JAMA, vol. 247, No. 12, pp. 1707–1714 (Mar. 28, 1982).

*Primary Examiner*—Leonard Schenkman
*Attorney, Agent, or Firm*—Banner & Witcoff LTD

[57] ABSTRACT

Metabolites of the D-isomer of propranolol show potent antioxidant activity, independent of β-blocker activity, that make them useful for the treatment of all conditions that can be treated by antioxidants, or any disease that is responsive to antioxidant treatment, for example, diseases or disorders of the cardiovascular system, heart failure, myocardial infraction, atherosclerosis, stroke, hypertension, ischemia/reperfusion injury an inflammatory processes.

9 Claims, 5 Drawing Sheets

4 - hydroxy-propranolol

The relative contribution of propranolol and its major metabolites to the in vivo antioxidant capacity in man.

D-PROPRANOLOL METABOLITES USEFUL FOR ANTIOXIDANT ACTIVITIES

This application claims priority to provisional application 60-012633, filed Mar. 1, 1996.

BACKGROUND OF THE INVENTION

1. Field of the Invention

This invention relates to the use of metabolites of propranolol which is a commercially available pharmaceutical compound used in the treatment of hypertension, angina and arrhythmias.

The metabolites, specifically, the metabolites of the D-isomer of propranolol, show potent antioxidant properties that make them useful for the treatment of all conditions that can be treated by antioxidants, or any disease that is responsive to antioxidant treatment, for example, diseases or disorders of the cardiovascular system, heart failure, myocardial infarction, atherosclerosis, stroke, hypertension, ischemia/reperfusion injury and inflammatory processes.

2. Description of the Prior Art

Certain pharmaceutical agents, such as β-blockers or calcium channel blockers, also possess antioxidant activity, which protect cellular and animal models against free radical injury; among the β-adrenergic receptor blocking drugs in clinical use, propranolol has been shown to protect against injury due to free radicals in vitro and in vivo. The important cardiovascular diseases in which beta blockade with D, L-propranolol may be beneficial induce angina pectoris, myocardial infraction, arrhythmias, hypertension and cardiomyopathy. The results from the BHAT study (*JAMA* 1982; 247:1707) leave little doubt that in patients with acute myocardial infarction, long term use of propranolol reduces reinfarction rates and improves survival; however, the exact mechanism remains unknown. In studying the antiatherogenic effects of propranolol, Chobanian et al., reported in 1985 that both L-propranolol, and its inactive isomer, D-propranolol, provided beneficial effects against diet-induced atherogenesis in a rabbit model. In their report, the authors attributed the beneficial effects of d-propranolol to non-specific membrane effects. (Chobanian et al., *Circ Res* 1985; 56:755–762). We found that relatively low dosage of D-propranolol (and D-L-propranolol) effectively limited Mg-deficiency-induced cardiomyopathy in rats and hamsters. (Weglicki et al., *Am J Cardiovasc Pathol.* 1992; 4:210–215). Using isolated membranes, my research team was the first group to report that propranolol has significant membrane antioxidant activity, which is unrelated to is β-blockade activity since D- and L-propranolol were equivalent. (Mak et al., *Pharmacol Res.* 1992; 25:25–30) Subsequently, this antioxidant activity provided cytoprotective effects in myocytes, endothelial cells, RBCs, and perfused rat hearts. (Kramer et al., *Ann NY Acad Sci* 1994; 723:180–196). Compared to the classic membrane chain-breaking antioxidant vitamin E., propranolol is at least 10-fold less potent as a membrane antioxidant. For most of those in vitro studies, relatively high levels of propranolol (up to 200 $\mu$M) are required to provide the membrane or cellular protective effects. There is a need to study the beneficial effects not related to beta blockade, that is, the antioxidant effects of D-propranolol.

SUMMARY OF THE INVENTION

Briefly, the present invention comprises the use of metabolites of propranolol, specifically the metabolites of the D-isomer of propranolol that have useful antioxidant activities. The D-isomer of propranolol does not have β-blocking activity and is therefore safer for use in conditions that can be treated by the administration of antioxidants.

In the present invention, it has been discovered that there are significant membrane antioxidant activities for some metabolites of propranolol, specifically and preferably the metabolites of the D-isomer of propranolol. The antioxidant potency of these preparations is great, about 2 orders of magnitude higher than that of propranolol. Experimental results indicate that the d-isomer of propranolol, which is pharmacologically inactive as a β-blocker displays potent antioxidant activity therefore, showing that the antioxidant activity is independent of pharmacological β-blocker activity.

Excessive free radicals in the cell membranes cause lipid peroxidative damage and protein oxidative damage. Antioxidants can neutralize these free radicals before they can cause this damage or may block the early chain reaction of peroxidation in the cell membranes.

Since free radicals are known to promote a number of cardiovascular and neurological diseases, including ischemia, reperfusion, aging, neurodegeneration, atherogenesis, inflammation and others, the use of the metabolites of the D-isomer of propranolol may provide beneficial effects as antioxidants where the increased free radical production is an important component of the disease pathogenesis.

It is an object of the present invention to provide uses of the metabolites of the d-isomer of propranolol as antioxidants for the treatment of conditions and diseases of the cardiovascular system, including heart failure, hypertension and related diseases.

It is another object of the present invention to provide uses of the metabolites of the D-isomer of propranolol as antioxidants for treatment of conditions and diseases such as neurological diseases, including ischemia, reperfusion, neurodegeneration, atherogenesis and acute and chronic inflammation.

These and other objects and advantages will be apparent from the detailed description which follows.

DETAILED DESCRIPTION OF THE INVENTION

Figure 1:
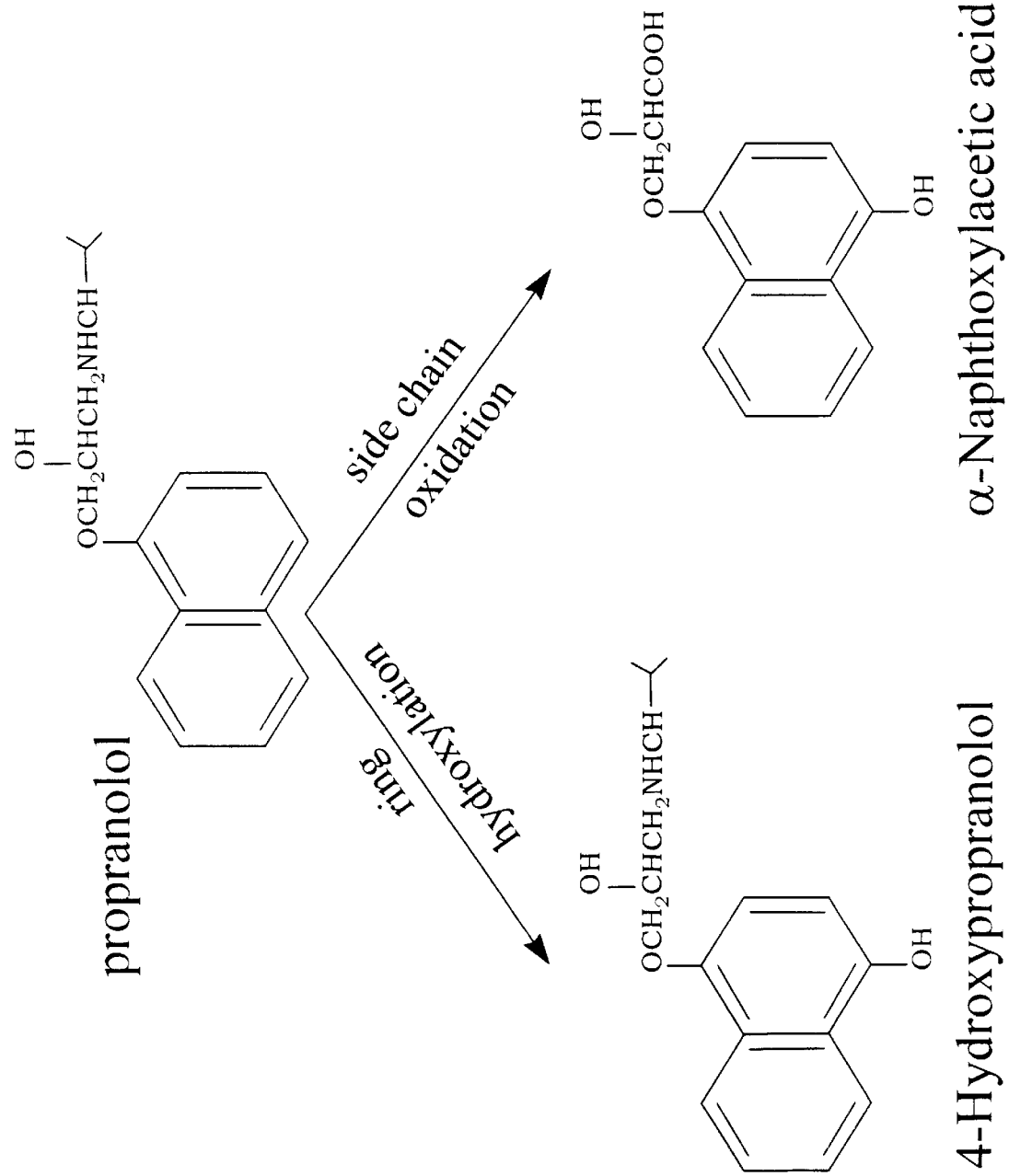
FIG. 1 is the major metabolic transformation of propranolol in man, adapted from Walle et al. *Clin Pharmacol Ther* 1994; 56: 127–132.

The use of beta blockers in the treatment of patients with heart problems has been a cornerstone of therapy for more than 30 years. In patients recovering from myocardial infarction treatment with propranolol resulted in significant increased survival. The BHAT trial confirmed the efficacy of such therapy but did not confirm the mechanism of action. Blockade of catecholamine effects on the heart can lower blood pressure and cardiac work. However, other unique physiochemical properties of beta blocker drugs have since been discovered in the past decade. The antioxidant effects of propranolol may provide cardiac protection against post myocardial infarction. Propranolol is highly soluble in lipid membranes of biological tissues and this characteristic correlates with antioxidant potency; also, the non-beta blocking form of D-propranolol is equally effective as L-propranolol. When the patient receives this drug, half of the dose is in the D form. When propranolol is given the bulk of the distribution into membranes of cardiovascular and other tissues is in the non-beta receptor portions of cell membranes; in these micro environments both forms of propranolol will provide equivalent antioxidant protection to the biomembranes. Indeed, the concentration of the drug in the bilayer exceeds that in the water soluble compartments of cells. It is in these lipid rich areas that vitamin E provides antioxidant protection as well. In those conditions where excessive free radicals are generated, the native antioxidant mechanisms of protection may be overwhelmed and tissue injury may result.

One principal mechanism of action of propranolol is as a chain breaking antioxidant just like Vitamin E. It is reported that tissue levels of Vitamin E were maintained when the beta blocking drug was incubated with the tissues during the exposure to excessive free radicals. In vivo, the circulating level of propranolol approaches only one micromolar, but this concentration only has minimal antioxidant potency in in vitro model membrane systems. In addition, Vitamin E is at least ten fold more potent than propranolol. Thus, for propranolol to produce an antioxidant mechanism of protection in patients after myocardial infarction it should be more potent in vivo by additional mechanisms. Prior studies have reported significant levels of hydroxylated propranolol in man. Although the circulating levels are one third those of propranolol, substantial antioxidant protection would be afforded if the antioxidant activity of this property metabolite was high. Indeed, hydroxylated propranolol is a hundred times more potent, than the parent compound. When the total contribution to antioxidant capacity in blood is calculated, about two thirds of the activity is due to it. Among the other metabolites side chain oxidation results in formation of alpha naphthoxylactic acid which also has moderate antioxidant activity along with naphthoxyacetic acid levels of these metabolites are ten times higher than propranolol and may account for one third of the antioxidant capacity. In man, we calculate that the contribution of propranolol only amounts to two percent of total antioxidant capacity.

The foregoing information about the metabolites of propranolol provides a rationale for treatment of diseases characterized by excessive free radical production in tissues of due to inflammatory processes that lead to loss of native antioxidant capacity. Examples of acute disorders include: reperfusion injury of the heart that may lead to myocardial infarction or similar injury of the brain during stroke; preservation of heart, liver, kidney and other organs for transplantation as a preservation solution or for prior treatment of the donor prior to harvesting the organ to be transplanted; treatment of acute lung dysfunction, such as pulmonary infarction or asthma with inflammatory components resulting in free radical excess; sun UV-induced skin damage. Chronic inflammation of viral or other causes may result in compromise of native antioxidant processes which could be prevented by therapy with D-propranolol metabolites. When non-beta blocking forms of these compounds are administered to all patients, substantially higher doses can be tolerated. Also asthmatics who cannot take any beta blockers due to bronchospasm can take high doses of non-beta blocking formulations.

In all of the above free radical mediated disorders, part of the cascade of biochemical events leading to injury may require free iron and copper to enable transformation of less potent radicals to highly toxic forms, such as the hydroxyl radical. Some cellular compartments may contain concentrations of these ions that may be inaccessible to potential therapeutic agents. However, propranolol is able to be concentrated in cellular compartments such as the lysosomes; it may alter the availability of iron and copper so that they do not contribute to injury. This adjunct property of propranolol-like molecules may also have important novel therapeutic efficacy by blocking release of pro inflammatory molecules contained within cellular vesicles requiring exocytic release when stimulated.

Propranolol, once consumed, is rapidly biotransformed into a number of metabolites. Of all the metabolites, 4-hydroxypropranolol (HOP) and α-naphthoxylactic acid (NAL) are formed in substantial quantities resulting from the hydroxylation of the ring or oxidation of the side chain shown in FIG. 1. In the rat, HOP accounts for more than 66% of the metabolic products as reported by Bargar et al. *Drug Metab Dispos* 1983; 1:266–272. Structurally, HOP's phenolic OH group could convert the metabolite to a "vitamin E-like" molecule—since the phenolic OH group is known to be essential for vitamin E's membrane, antioxidant activity and hydroxylation of propranolol's naphthylene ring which should greatly its antioxidant potency. In accordance with the present invention, it is shown that HOP is 100-fold more potent than propranolol as an antioxidant. This potency is in the same order of magnitude as vitamin E. A more than 2-fold increase in potency is seen with HOP over Trolox which is a water soluble form of vitamin E.

Figure 3:
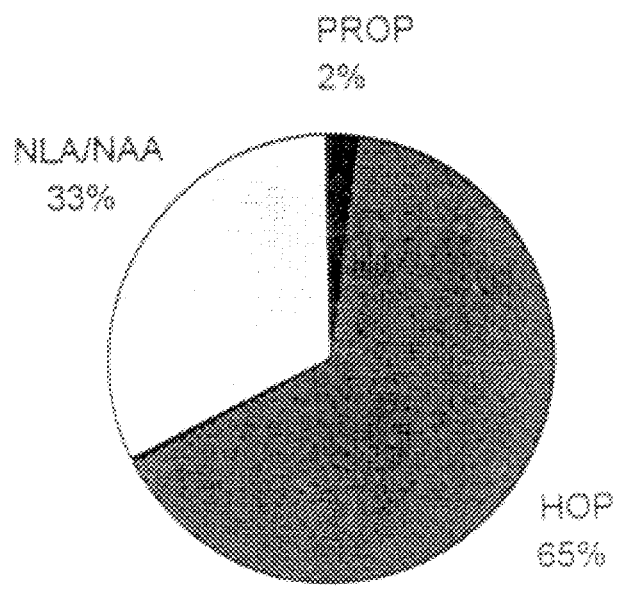
FIG. 3 graphically represents the relative contribution of propranolol and its major metabolites to the in vivo antioxidant capacity in man.

Metabolites of propranolol include 4-OH-propranolol and α-naphthoxylacetic acid (NLA) as shown in FIG. 1. As long as the naphthoxyl linkage is maintained, it appears that much of the antioxidant activity of NLA and NAA is comparable to that of propranolol. Since the plasma concentration of combined NLA/NAA can be ten-fold higher than that of propranolol, NLA/NAA may make a significant contribution to the total antioxidant effective in vivo. Since certain levels of metabolites reach significant levels after propranolol administration, the metabolites provide a much higher antioxidant capacity than the nonmetabolized propranolol alone. Accordingly, based on the relative plasma concentration of propranolol and its metabolites in man (at 100 mg daily dose of D, L propranolol), an estimate of the calculated respective contribution of total antioxidant capacity from each metabolite is shown in FIG. 3.

The D- and L-propranolol have about the same antioxidant potency. Clinically prescribed propranolol is a 50/50 mixture of D- and L-isomers. However, in accordance with the present invention, the metabolites have a much greater potency.

Figure 2:
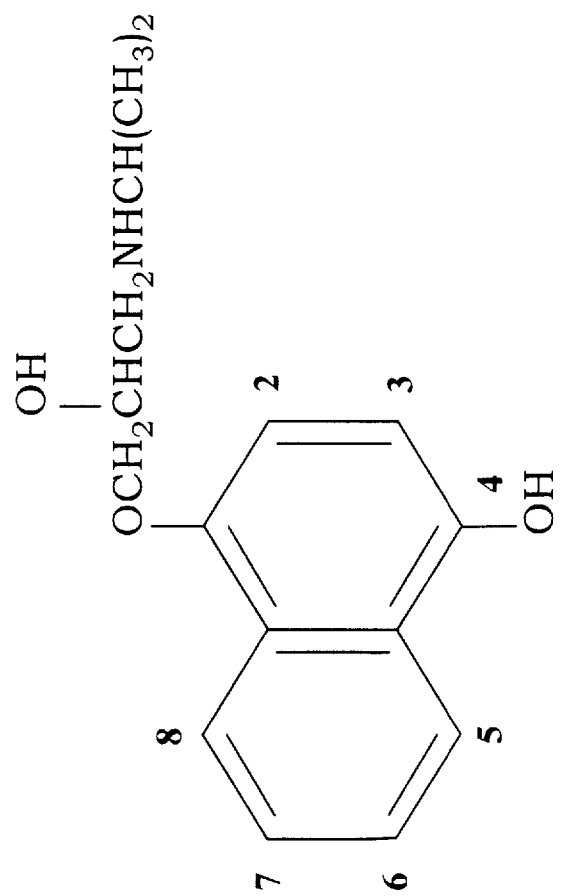
FIG. 2 shows the chemical structure of 4-OH-propranolol acid.

FIG. 1 shows the transformation of propranolol in man. If administered, L-propranolol and D-propranolol will transform to 4-hydroxypropranolol (FIG. 2) and α-naphthoxylactic acid which, in accordance with the present invention, have increased antioxidant activity over propranolol. If the metabolites are to be synthesized, the starting material should be D-propranolol so that the β-blocking activity is negated.

The metabolites can be effective in treating all diseases and conditions disclosed herein including those that can be treated by inhibition of free radicals and those that can be treated by administration of antioxidants.

The dosage of the metabolites of D-propranolol will vary depending upon the condition of being treated and the state of the subject, but generally may be in an amount sufficient to achieve the desired effect of inhibiting the flow of free radicals or any other antioxidant effect. For specific treatment of a condition or disease, such as ischemia or reperfusion injury, one skilled in the art could determine dosage by appropriate medical and pharmacokenetic standards. Typically, one may administer a sufficient amount of D-propranolol, taken orally or intraveneously, to treat or prevent any disease that is responsive to antioxidant therapy or which is contributed to by free radical activity. Dosages typically may be from about 500 mg to about 1000 mg per day. The preferred amount is the amount sufficient to inhibit free radical activity or that causes a response to the antioxidant therapy. As contemplated by this invention, the metabolites of D-propranolol can be embodied in pharmaceutical dosage formulations containing from about 500 mg to 1000 mg per day. The metabolites of D-propranolol and their pharmaceutically acceptable salts can be administered internally, for example, parenterally or enterally, and conventional pharmaceutical dosage forms. For example, they can be incorporated in conventional liquid or solid vehicle such as water, gelatin, starch, magnesium stearate, talc, vegetable oils, and the like to provide tablets, elixirs, capsules solutions emulsions and the like according to acceptable pharmaceutical practices. Further, the metabolites of D-propranolol can be administered topically, instilled in the eye, aspirated and administered vaginally or rectally.

Applicant, in setting forth the disclosure of the above specification, has cited the teachings of various articles. Such citations are meant to incorporate the teachings of these references for completeness of the disclosure.

The present invention is explained in greater detail in the examples which follow. These examples are intended as illustrative of the invention, and are not to be taken as limiting thereof.

EXAMPLE 1

Figure 4:
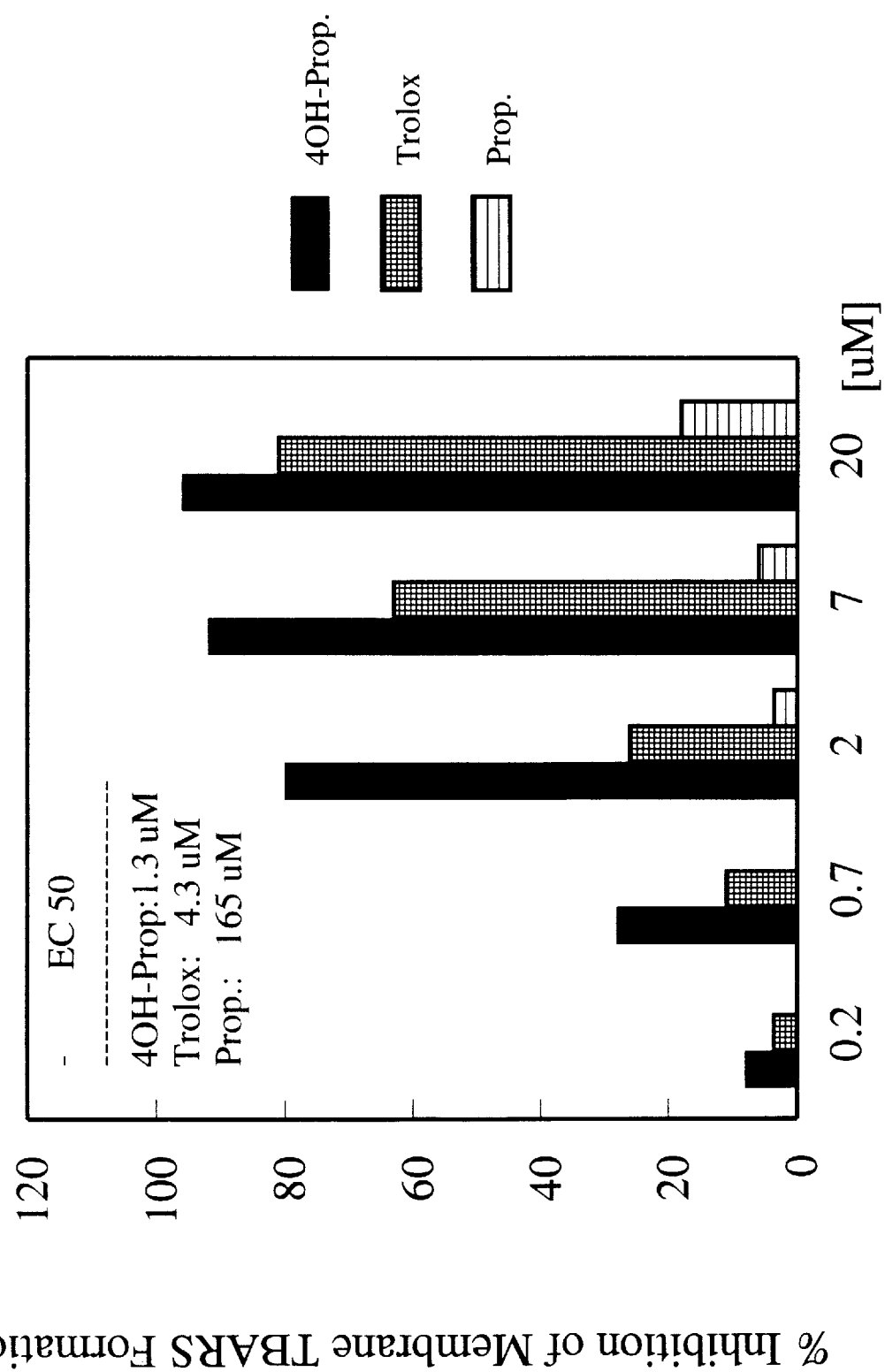
FIG. 4 graphically represents the inhibitory effects of propranolol, 4-HOP and vitamin E (Trolox) against free radical-induced lipid peroxidation in Hepatic microsomal membranes the $EC_{50}$ is the effective concentration which inhibits 50% of the membrane lipid peroxidation. Microsomes (0.2 mg/ml) were pre-incubated with agents for 15 minutes followed by 20 minutes Fe-ADP and DHF exposures at 30° C. Samples were assayed for the peroxidation product malondialdehyde (TBARS) formation and expressed as percent inhibition relative to the controls.

To test the relative antioxidant potency of propranolol (PROP), Trolox (vitamin E analogue) and 4-hydroxypropranolol (HOP), the following in vitro assay system was used: microsomal membranes were isolated from Hepatic tissue by differential concentration and suspended in buffer, preferably PBS, at a concentration of 0.2 mg of membrane protein per milliliter of buffer. In FIG. 4, the concentrations of the three agents, 4-hydroxypropranolol, Trolox and propranolol were added from 0.2 to 20 $\mu$M levels for 15 minutes at 4° C. After preincubation, free radicals were generated by reacting dihydroxyfumarate with iron-adenine diphosphate (Fe-ADP) in each tube for 20 minutes at 30° C. to create superoxide and hydroxylradicals of a standard amount (see Mak and Weglicki, *Methods in Enzymology*, 234:620–630, 1994). The end product of peroxidation of membranes (TBARS) was assayed and the present inhibition of TBARS is plotted on the vertical axis of FIG. 4 4-HOP was found to inhibit peroxidation by 50% at 1.3 $\mu$M, whereas Trolox was only effective at 4.3 $\mu$M and propranolol only at 165 $\mu$M, confirming more than 100-fold greater antioxidant potency of 4-HOP.

EXAMPLE II

The procedure of Example I was followed with the following test agents: 4-hydroxypropranolol, carvedilol, Trolox, a water soluble form of vitamin E and propranolol.

Figure 5:
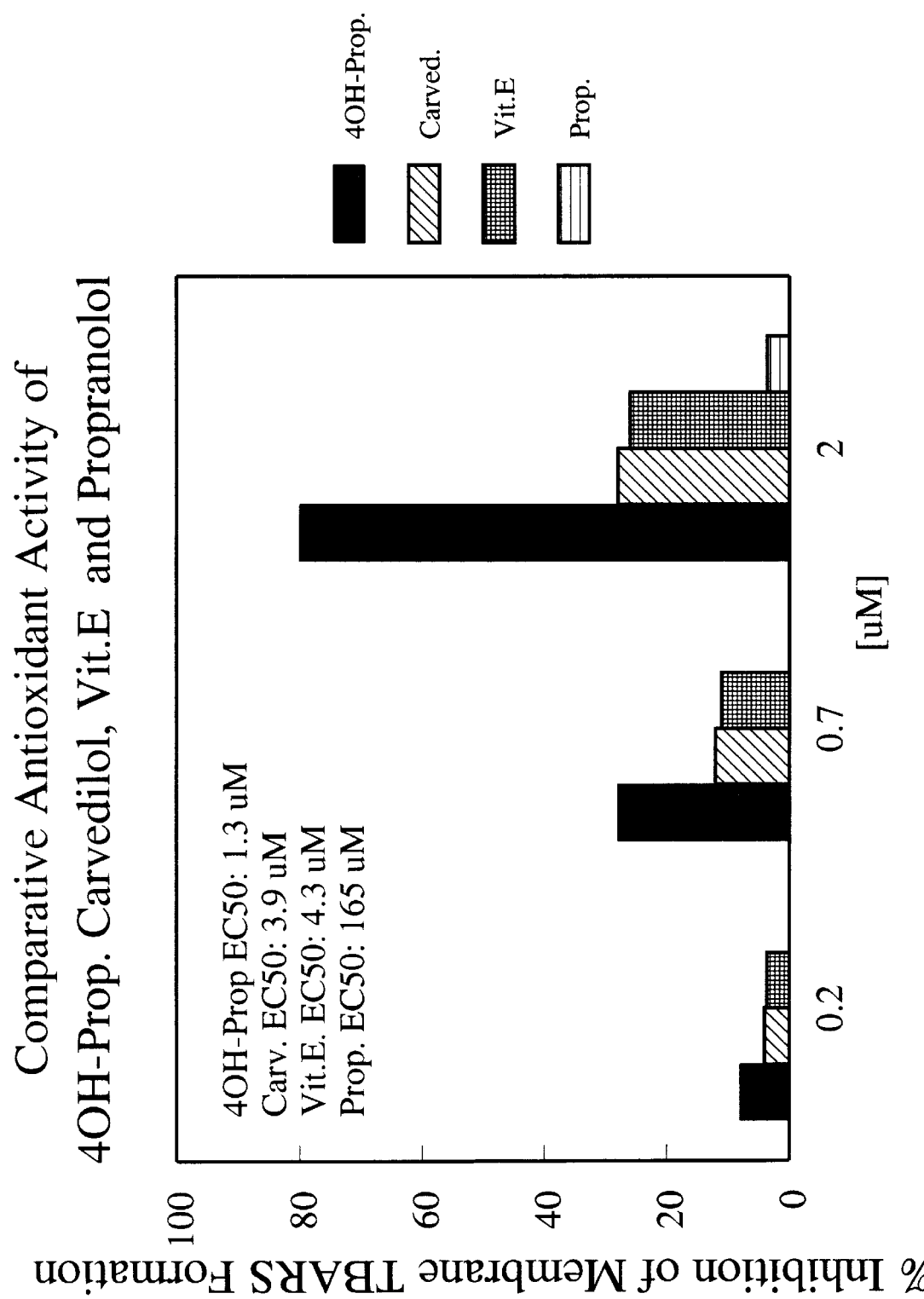
FIG. 5 graphically represents the inhibitory effects of 4-HOP, carvedilol, vitamin E (Trolox) and propranolol.

In FIG. 5, the comparative antioxidant inhibitory effects of these agents against free radical-induced lipid peroxidation in microsomal membranes were obtained. Hepatic microsomal membranes (Co 2mg/ml) were pre-treated with each agent for 20 minutes before additional of Fe-ADP and DHF, which is a superoxide anion driven, iron-catalyzed, oxy-radical system described in Mak & Weglicki *Methods of Enzymology* 234: 620–630, (1994). After 20 minutes of incubation at 30° C., samples were assayed for malondialdehyde (TBARS) formation. The data are expressed as percent inhibition relative to the non-drug treated controls as shown in FIG. 5.

The subject methods and metabolites of D-propranolol described herein provide methods for treating conditions and diseases which can be treated by antioxidant agents. The high potency of antioxidant metabolites of propranolol of the present invention show superior antioxidant activity to conventional antioxidant compounds. The method comprises administering to a subject in need thereof, a sufficient amount of metabolites of D-propranolol having antioxidant activity, namely, those selected from the group consisting of 4-hydroxy propranolol, α-naphthoxylactic acid and α-naphthoxyacetic acid.

The invention now being fully described, it may be apparent to one of ordinary skill in the art that many changes and modifications can be made thereto without departing from the spirit or scope of the appended claims.

What is claimed is:

1. A method of producing an antioxidative effect to a patient in need thereof which comprises administering to said patient an effective amount of a metabolite of D-propranolol said metabolite being inactive as a beta blocker.

2. The method of claim 1 wherein the metabolite is selected from the group consisting of 4-hydroxypropranolol, α-naphthoxylactic acid, and α-naphthoxyacetic acid.

3. The method of claim 1 wherein the amount of the metabolite administered to the patient is about 500 to 1000 mg per day.

4. A method of producing an antioxidative effect in a patient suffering from a disease or disorder of the cardiovascular system comprising administering to said patient a metabolite of D-propranolol, said metabolite being inactive as a beta blocker.

5. The method of claim 4 where in the metabolite is selected from the group consisting of 4-hydroxy propranolol, α-naphthoxylactic acid, and α-naphthoxyacetic acid.

6. A method of producing an antioxidative effect in a patient in need of free radical activity inhibition comprising administering to said patient a metabolite of D-propranolol, said metabolite being inactive as a beta blocker.

7. The method of claim 6 wherein the metabolite is selected from the group consisting of 4-hydroxy propranolol, α-naphthoxylactic acid, and α-naphthoxyacetic acid.

8. A method of producing an antioxidative effect in a patient suffering from a disease or condition selected from the group consisting of heart failure, heart attack, coronary infarction, ischemia/reperfusion injury, cardiovascular degeneration, neurodegeneration or arteriosclerosis and inflammatory process comprising administering to said patient a metabolite of D-propanolol, said metabolite being inactive as a beta blocker.

9. The method of claim 8 wherein the metabolite is selected from the group consisting of 4-hydroxy propranolol, α-naphthoxylactic acid, and α-naphthoxyacetic acid.

* * * * *